United States Patent [19]

Hale

[11] 4,337,431

[45] Jun. 29, 1982

[54] EDDY CURRENT TEST APPARATUS FOR ANNULAR WELDS

[75] Inventor: John C. Hale, Thurso, Scotland

[73] Assignee: United Kingdom Atomic Energy Authority, London, England

[21] Appl. No.: 19,595

[22] Filed: Mar. 12, 1979

[30] Foreign Application Priority Data

Mar. 13, 1978 [GB] United Kingdom ............... 9849/78

[51] Int. Cl.³ ..................... G01N 27/72; G01N 27/82
[52] U.S. Cl. ..................................... 324/220; 324/238
[58] Field of Search ............. 324/220, 222, 225, 237, 324/238, 241, 242, 243; 318/647; 390/686

[56] References Cited

U.S. PATENT DOCUMENTS 3,419,797 12/1968 Libby ................................ 324/220
3,875,502 4/1975 Neumaier .......................... 324/241
4,134,067 1/1979 Woodbury ........................ 324/241

Primary Examiner—Gerard R. Strecker
Assistant Examiner—Walter E. Snow
Attorney, Agent, or Firm—Larson and Taylor

[57] ABSTRACT

Non destructive test apparatus for the inspection of annular welds, such as the tube/tube sheet welds of a tube-in-shell heat exchanger, using eddy current techniques. The apparatus comprises a rotatable probe assembly having a pair of sensors for interrogating the weld, bridge means for comparing the signals produced by the sensors and electronic circuitry arranged to combine the differential of the signals with a simple voltage locus signal derived from a sine/cosine potentiometer associated with the probe assembly drive and to feed the combination signal to an oscilloscope.

3 Claims, 7 Drawing Figures

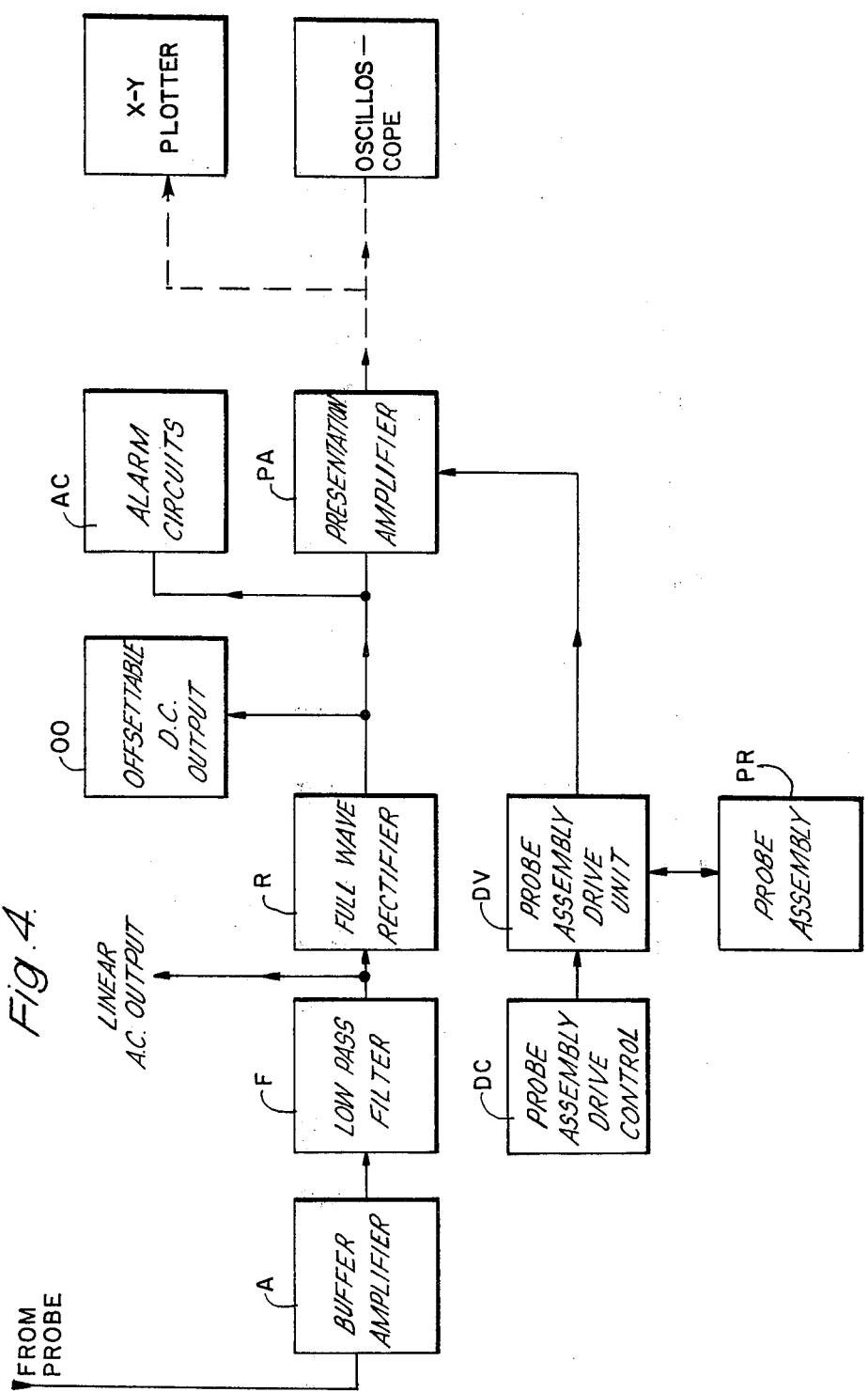

EDDY CURRENT TEST APPARATUS FOR ANNULAR WELDS

BACKGROUND OF THE INVENTION

This invention relates to non-destructive test apparatus for the inspection of annular welds using eddy current techniques.

The use of eddy current techniques for examining materials is well known; flaws in a material affect electrical resistivity and magnetic permeability and are thereby readily detected by variations in induced eddy currents. One technique, for example, as disclosed in British Pat. No. 1058862, comprises comparing the signals derived from a pair of spaced eddy current sensors arranged to interrogate the material and displaying the flaw indicating differential signal on an oscilloscope.

It has recently been proposed to use the technique for the inspection of annular tube/tube sheet welds of a tube-in-shell heat exchanger, the apparatus comprising a rotatable eddy current probe assembly having a pair of sensors with means for rotating the sensors about a weld bead and means for displaying the differential of the signals produced by the sensors, the differential being produced by means of a balanced bridge. When both the sensors are interrogating normal weld metal the random variation of the strength of the differential signal caused by multi-metal composition and rough surface tends to average out towards a mean balance so that an oscilloscope display of an acceptable weld presents a randomly oriented trace about a central point. A flaw or defect in the weld bead will result in a deviation in the trace from the central point and appears as a spike or finger extending from the central area of the display.

The spike or finger will indicate the location of the flaw in the weld bead and this location will be determined by reference to the position of the appropriate sensor. For a good weld the trace on the display can resemble a jumble or tangle of string, the complex nature of the trace being due to migration of the beam spot under the influece of differing amplitude and phase information as the probe interrogates different parts of the weld bead. The interpretation of such a trace is very difficult and it is an object of the present invention to provide apparatus which will give a pictorial display representing an annular weld and upon which is superimposed the position and relative size of any defect present in the weld bead.

SUMMARY OF THE INVENTION

According to the invention in an improved non-destructive test apparatus for inspecting annular welds using eddy current techniques, the apparatus being of the kind comprising a rotatable eddy current probe assembly having a pair of sensors for interrogating the weld and means for comparing and displaying the differential of the signals produced by the sensors, the improvement resides in associated electronic circuitry which is arranged to combine the differential signal with a simple voltage locus signal derived from a sine/-cosine potentiometer associated with the probe assembly drive and to feed the combination signal to display or storage means. In operation, when the probe assembly is rotated about the weld bead the output differential signal provides a component for the display of a diagram of the weld, the signal in combination with a signal derived from the potentiometer producing a circular 'map' of the weld with the defect signals superimposed as vectors. The vectors are formed normal to the tangent of the circle at the precise location of the defect position and of an amplitude related to the strength of the defect signal.

Invention will also reside in a method of inspecting an annular weld comprising interrogating the weld with a first eddy current sensor and comparing the signal derived from the sensor with a reference signal derived from a second sensor arranged to interrogate a weld, combining the resultant differential signal with a simple voltage locus signal derived from a sine/cosine potentiometer associated with the probe assembly drive and feeding the combined signal to display or storage means. The second sensor can be arranged to interrogate the same weld as that interrogated by the first sensor or to interrogate a second weld. By arranging for the second sensor to interrogate a second weld which is known to be sound complexity caused by both sensors simultaneously sensing a flaw is largely avoided.

DESCRIPTION OF THE DRAWINGS

A constructional embodiment of the invention is described, by way of example, with reference to the accompanying diagrammatic drawings wherein:

FIGS. 4, 5, 6 and 7 illustrate electronic circuitry.

DESCRIPTION OF THE PREFERRED EMBODIMENT

Figure 1:
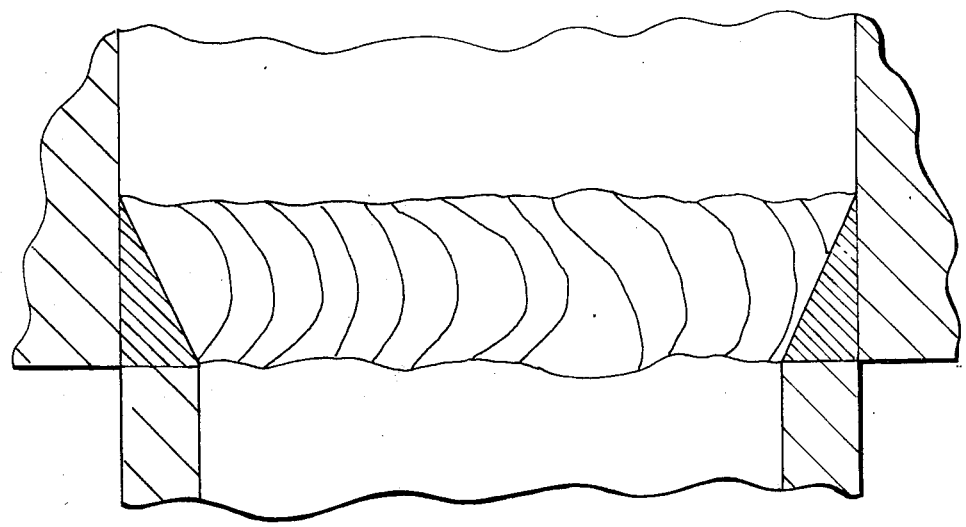
FIG. 1 is representative of a tube to tube plate weld of a heat exchanger.
Figure 2:
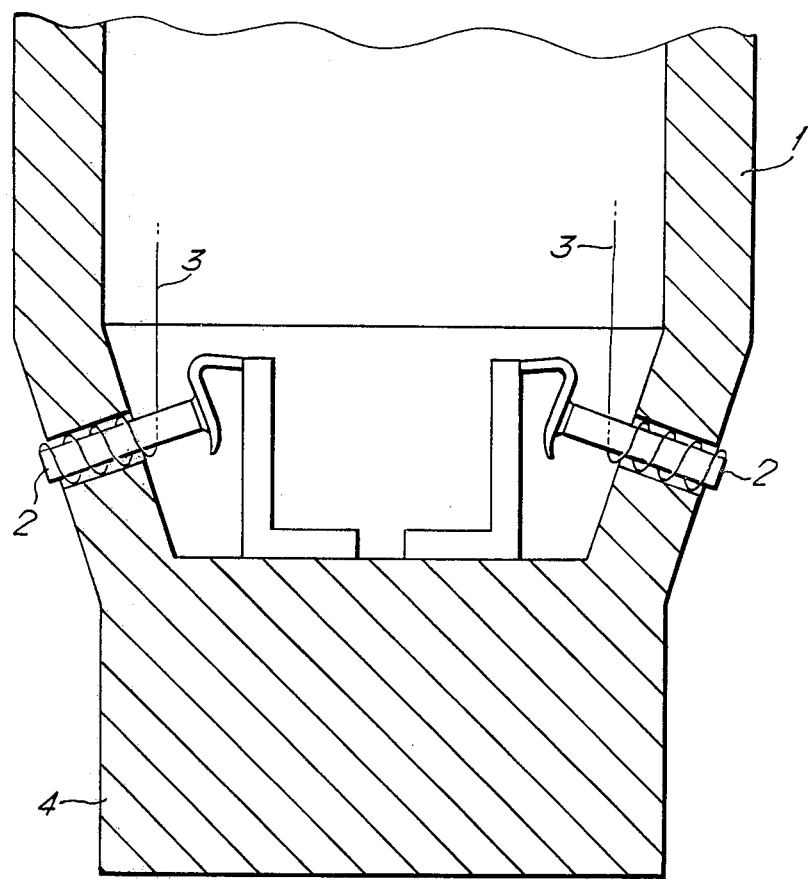
FIG. 2 is a section through an eddy current probe assembly.

In FIG. 1 there is shown a section of a tube to tube plate weld which is to be inspected for flaws. The apparatus for inspecting the annular weld bead comprises an eddy current probe assembly shown diagrammatically in FIG. 2 comprising a cylindrical body 1 having two diametrically opposed sensors 2 of conventional kind with leads 3 attached thereto for extending to electronic circuitry. The body has a cylindrical extension 4 of smaller diameter for rotatably engaging the bore of the heat exchange tube. The sensors are included in conventional bridge circuitry to produce a differential signal in ac wave form having amplitude dependent upon the overall balance of the probe assembly circuit so that significant defects in the weld produce a noticeable unbalance of the circuit and hence a considerable increase in the out-of-balance signal amplitude. The probe assembly is driven by a shaded pole capacitor start motor running on 50 Hz 230 v through a reduction gearbox having a reverse facility to enable the sensors to scan the weld in each direction. As discussed below, the electronic circuitry is arranged to combine the bridge balance signal with the output signal of a sine/-co-sine potentiometer on the automatic probe assembly drive and the combination signal is fed to a storage oscilloscope of an X-Y plotter. Alternatively the signal can be stored on magnetic tape.

Figure 3:
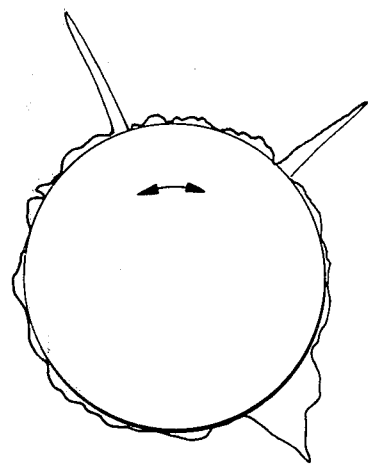
FIG. 3 is a view of an oscilloscope display of a weld examination.

In operation, when the probe assembly is rotated about the weld bead the output differential signal of the sensors is used to display a diagram of the weld, the signal in combination with the motor driven potentiometer producing a circular 'map' of the weld with the defect signals superimposed as vectors. The vectors are formed normal to the tangent of the circle at the precise location of the defect position and of an amplitude related to the strength of the defect signal as shown in FIG. 3.

Figure 5:
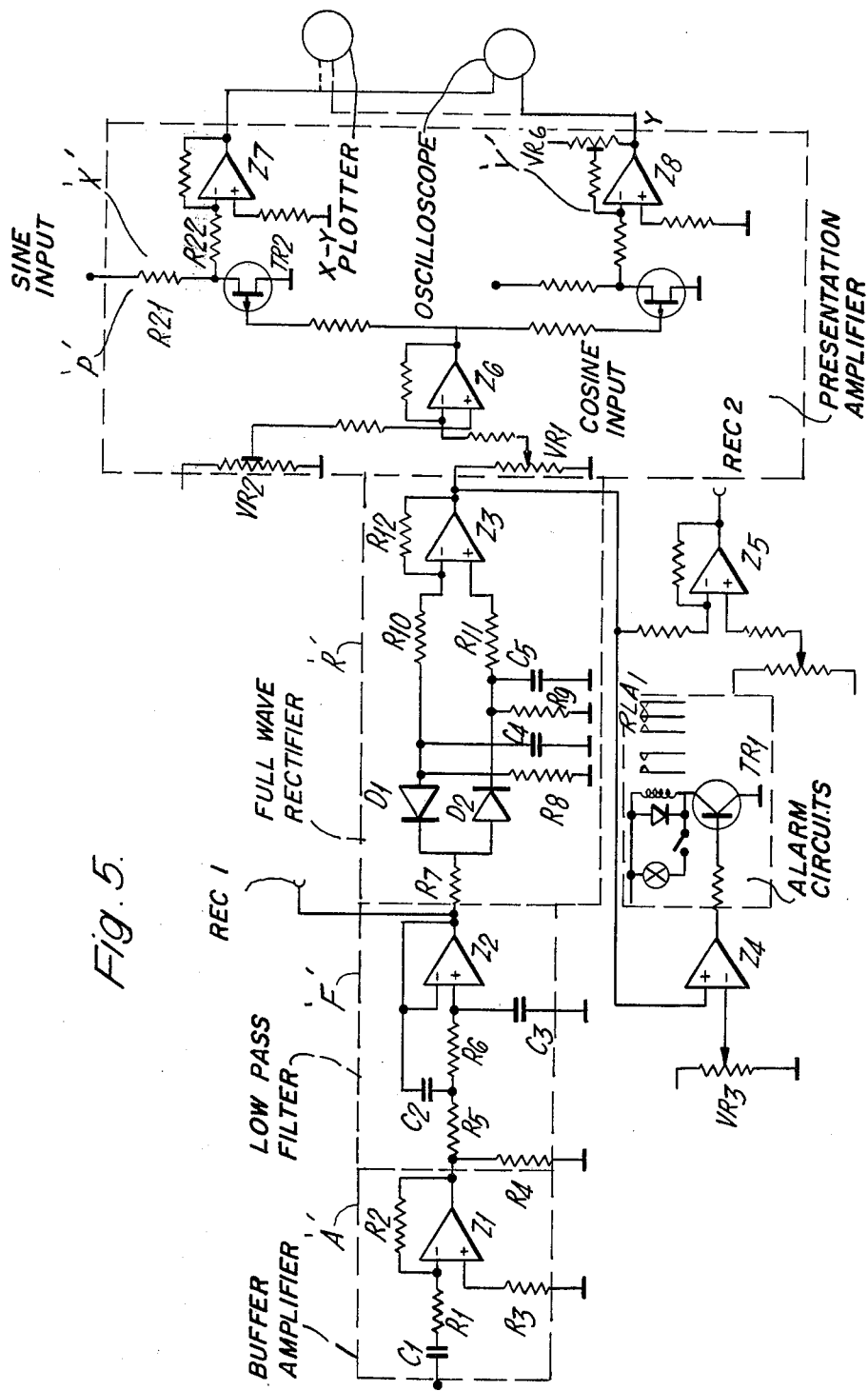
Figure 6:
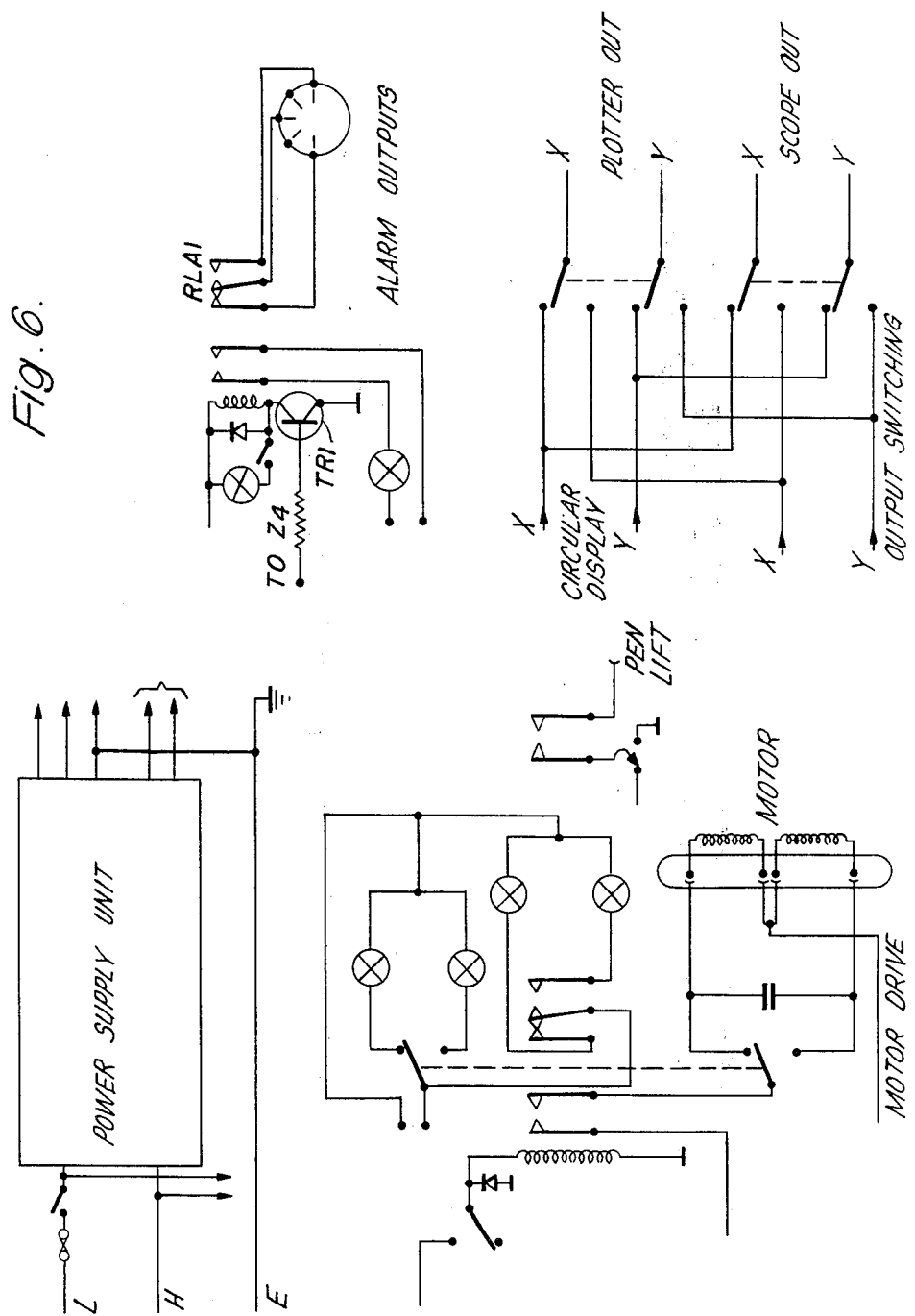
Figure 7:
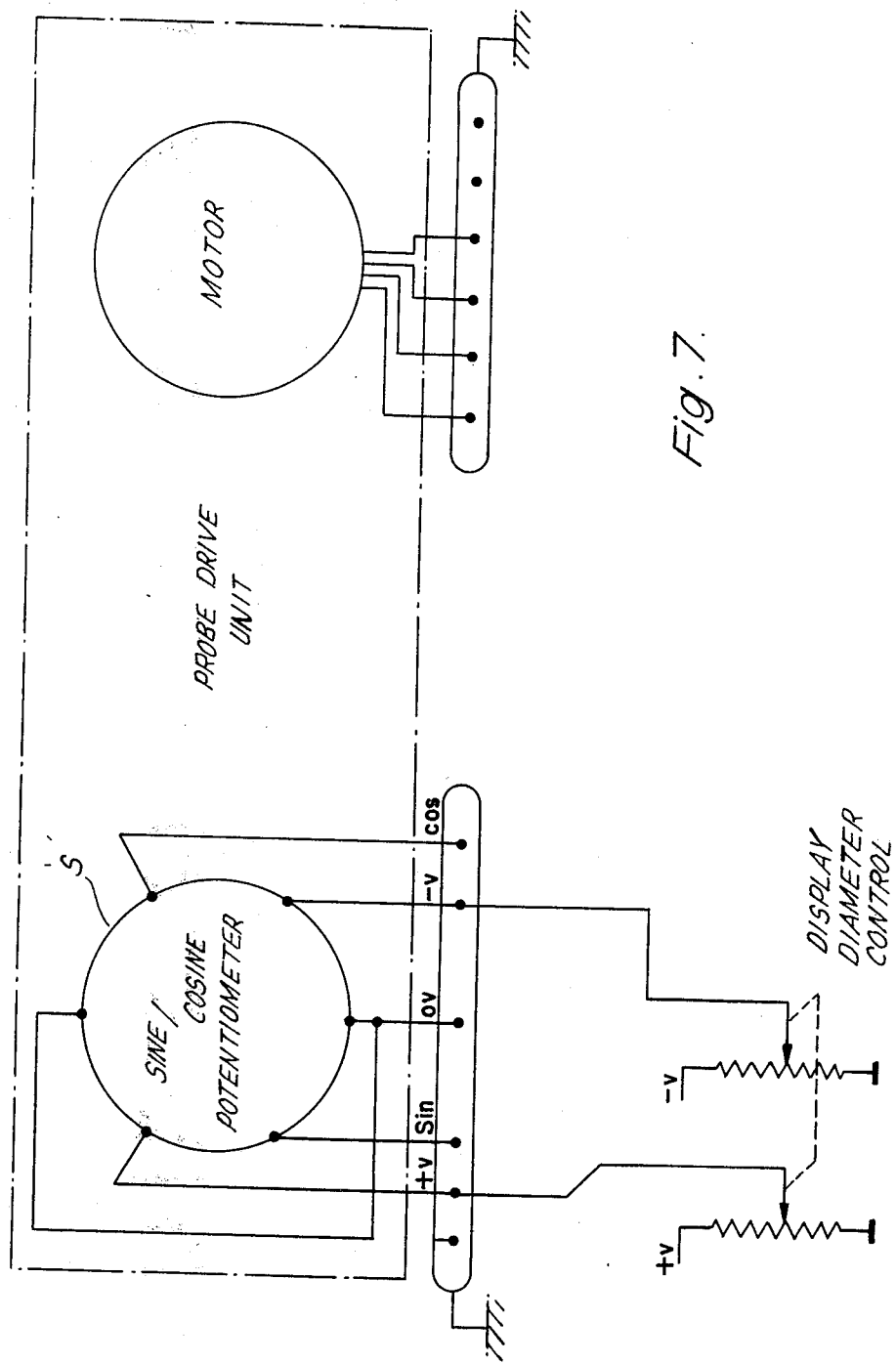

FIG. 4 is a block diagram illustrating the basic components of the electrical circuitry which is shown in greater detail in FIGS. 5, 6 and 7. As shown in FIG. 4 the basic components of the system comprise a buffer amplifier A connected through a low pass filter F to a full wave rectifier R. The output of the full wave rectifier R is connected to an offsettable D.C. output 00, to alarm circuits AC, and to a presentation amplifier PA. The latter also receives an input from a probe assembly drive unit DU connected to probe assembly PR and controlled by a probe assembly drive control circuit DC. The output of presentation amplifier PA is connected to an X-Y plotter or an oscilliscope as indicated.

FIGS. 4, 5, 6 and 7 illustrate the electronic circuitry. With reference to the buffer amplifier 'A' shown in FIG. 5 of the drawings, $R_1$, $R_2$, $R_3$, $C_1$, $Z_1$, from a simple ac coupled inverting amplifier with a gain of 100. This simply buffers the differential signal and provides sufficient gain to drive the filter stage.

The differential signal is a complex sinusoid whose phase and amplitude varies with a degree of out of balance of the ac bridge detector and $R_4$, $R_5$, $R_6$, $C_2$, $C_3$, and $Z_2$ form a low pass filter 'F' with a corner frequency of 300 Hz, thus filtering out the excitation frequency (35 KHz) but allowing the 'change of amplitude' signal to pass to the next stage.

The low frequency signal from the filter is rectified by the full wave rectifier 'R' $R_7$, $R_8$, $R_9$, $R_{10}$, $R_{11}$, $R_{12}$, $D_1$, $D_2$, $C_4$, $C_5$, and $Z_3$, producing a dc voltage whose value is dependent on the out of balance signal from the bridge. This voltage is used to control the display and alarm stages, as illustrated. The alarm circuit indicated in FIG. 5 is shown in more detail in FIG. 6.

The circular display is derived from the sine-cosine potentiometer 'S' ganged to the probe assembly drive unit (FIG. 7) and when sine and cosine vectors are applied to the X-Y coordinate system (the sine and cosine input signals to the drive amplifiers being shown in FIG. 5) the result is a circle, the diameter of which is dependent on the magnitude of equal vectors and adjustable by the display control shown in FIG. 7. The 'defect' lines are produced by increasing equally the magnitude of the sine-cosine vectors, in effect drawing part of the radius to a larger circle. This is achieved as follows:

With reference the X-drive amplifier 'X' shown in FIG. 5 the field effect transistor TR2 is used as a voltage controlled resistor. As the voltage on the gate increases with respect to the drain, the effective resistance of the source-drain channel increases. $R_{21}$ and TR2 form a potentiometer 'P' (FIG. 5). The larger the signal on the gate of TR2 the larger the sine voltage present at the junction of $R_{21}$ and $R_{22}$ which feeds the output amplifier 'X'. VR2 places a bias on the gate of TR2 so that it operates in its linear region.

The Y-drive amplifier 'Y' is identical except for VR6 which is used to correct any gain differences between $Z_7$ and $Z_8$.

Thus, if the defect signal is applied to both amplifiers simultaneously, the magnitude of the sine and cosine vectors will be increased by an equal factor, moving the spot on the screen radially outward. The level of modulation may be set by VR1. $Z_6$ feeds the fet bias voltage and the defect signal to both amplifiers.

In addition to the X-Y drive, two recorder outputs are provided for use with Y-T recorders. These outputs are: the change in amplitude signal from the low-pass filter and the dc defect signal (positive-going) from the ac rectifier and the two recorder outputs are indicated at Rec 1 and Rec 2 in FIG. 5. This latter signal, i.e., the dc defect signal, is buffered by $Z_5$ which also has a recorder offset bias adjustment.

Two X-Y delay outputs are connected as shown in FIG. 6 so that an X-Y plotter may be used in addition to the storage oscilloscope or, alternatively, the display may be recorded on two tracks of an FM tape recorder. These outputs are switched so that, without disconnecting any leads, the original phase/amplitude signal may be display or recorded.

A pen-lift command (see FIG. 6), controlled by the motor drive run/stop switch, is available for use with X-Y pen recorders.

$Z_4$ is a voltage comparator and when the output from the ac rectifier exceeds the reference set by $VR_3$, $TR_1$ is turned on closing $RLA_1$. There are three alarm outputs: a lamp, an audible alarm (which may be silenced if so desired) and one set of changeover contacts. This threshold detector provides a simple go-no-go system and is dependent on defect size.

The motor drive circuit, which is shown in the lower right hand corner in FIG. 6 is merely a simple switching arrangement to control the movement and direction of the motor and indicator lamps are provided for fast appraisal of motor status.

A power supply unit and associated connections are illustrated in the upper left hand corner of FIG. 6.

The reversible motor drives the probe assembly through a shaft which is connected to the top of the probe assembly by means of a quick release coupling and the sine cosine potentiometer is mounted on the drive shaft.

In an alternative construction the probe drive includes a universal coupling to accommodate non-alignment of the probe assembly with the weld bead under inspection, and there is an automatic cycle reverse monoswitch to provide automatic control of scanning in each direction.

I claim:

1. Eddy current test apparatus for inspecting annular welds, said test apparatus comprising:
   a rotatable eddy current probe assembly comprising a pair of diametrically opposed sensors for interrogating the weld and for producing signals in accordance therewith,
   a motor for driving said probe assembly,
   means, including a bridge circuit, for comparing the signals produced by said sensors and for providing an out-of-balance signal based on a comparison of said signals,
   a sine/cosine potentiometer, driven by said motor so that said potentiometer moves in phase with the probe assembly, for producing electrical output signals in accordance with the position of said probe assembly, said output signals comprising a sine signal and a cosine signal,
   a display means, including an x-input and a y-input, for producing a positional indication of the angular location of the potentiometer and thus of said probe assembly responsive to said electrical output signals from said sine/cosine potentiometer, first amplifier to which said sine signal is fed and including an output connected to the x-output or y-output of said display means, a second amplifier to which said cosine signal is fed and including an output connected to the y-input or x-input of said display means, electronic circuit means for combining directly and in real time the out-of-balance signal with the sine signal by feeding the out-of-balance signal to an input of said first amplifier and for combining directly and in real time the out-of-balance signal with the cosine signal by feeding the out-of-balance signal to an input of said second amplifier, the magnitude of the outputs of the first and second amplifiers being controlled by the combination of signals fed thereto, and means for correcting any differences in the gain characteristics of said first and second amplifiers, said display means including means for combining the input signals at said x-input and said y-input to produce a combined display signal in real time in which the angular position of the display is determined solely by the signals from the sine/cosine potentiometer and in which the radial amplitude of the display signal is determined solely by said out-of-balance signal.

2. Apparatus according to claim 1 wherein the display comprises an oscilloscope.

3. Apparatus according to claim 1 wherein the display comprises an X-Y plotter.

* * * * *